United States Patent [19]

Tarro

[11] Patent Number: 5,747,643
[45] Date of Patent: May 5, 1998

[54] ANTIGENIC REGIONS OF TUMOR-LIBERATED PARTICLES (TLP) COMPLEXES AND ANTIBODIES AGAINST THE SAMES

[75] Inventor: Giulio Tarro, Naples, Italy

[73] Assignee: Instituto Farmacoterapico Italiano S.p.A., Italy

[21] Appl. No.: 351,284
[22] PCT Filed: Jul. 1, 1993
[86] PCT No.: PCT/IT93/00069
  § 371 Date: Dec. 22, 1994
  § 102(e) Date: Dec. 22, 1994
[87] PCT Pub. No.: WO94/01458
  PCT Pub. Date: Jan. 20, 1994

[30] Foreign Application Priority Data
  Jul. 3, 1992 [IT] Italy ................. RM92A0506

[51] Int. Cl.$^6$ ............. A61K 38/04; C07K 5/00; C07K 7/00; C07K 16/00
[52] U.S. Cl. ............ 530/329; 530/387.7; 530/388.8; 424/277.1; 435/7.23
[58] Field of Search ............... 530/300, 328, 530/329, 350, 806, 810, 812, 828; 435/7.23; 436/64; 424/277.1

[56] References Cited

FOREIGN PATENT DOCUMENTS 0283443 of 0000 European Pat. Off.

OTHER PUBLICATIONS

Harlow et al Antibodies: A Laboratory Manual, Chapter 5, pp. 55–136, Cold Spring Harbor Laboratroy, 1988.
"Human Tumor Antigens Inducing in vivo Delayed Hypersensitivity and in vitro Mitogenic Activity" by Tarro et al.; Oncology 40, pp. 248–254 (1983).

Primary Examiner—Lila Feisee
Assistant Examiner—Yvonne Eyler
Attorney, Agent, or Firm—Brumbaugh, Graves, Donohue & Raymond

[57] ABSTRACT

Peptides comprised within the 100 KDa protein of the TLP complex (i.e., released proteins from tumors) having antigenic activity as well as antibodies thereof, able to react with TLP for diagnostic and clinical purposes.

4 Claims, 4 Drawing Sheets

ANTIGENIC REGIONS OF TUMOR-LIBERATED PARTICLES (TLP) COMPLEXES AND ANTIBODIES AGAINST THE SAMES

SPECIFICATION

This invention relates to peptide regions of the human TLP proteic complexes (proteins released from tumors) with antigenic activity, as well as to antibodies reacting with such proteins, to be used for diagnostic and clinical purposes.

TLP complexes are proteic complexes present in human tumor cells, particularly in lung carcinoma cells; among the TLP proteins a 214 KDa protein is described (Tarro G., "Oncology", 40, 248-253, 1983). TLPs are isolated from tumoral tissues, as described in the EP 283 433, the description thereof is incorporated herein as reference. It is very useful to have diagnostic assays to identify such complexes, or fractions thereof, from crude lung extracts.

Author's attempts to obtain specific antibodies against whole TLP's did not succeed. Therefore it is important to identify TLP antigenic regions (epitopes) and raise antibodies thereto, in order to obtain specific reactants.

The author of the present invention has identified peptide sequences of the TLP 100 KDa protein having antigenic activity, has obtained specific antibodies and has demonstrated that said antibodies reacted specifically with TLPs from lung carcinomas.

Accordingly, an object of this invention is an antigenic peptide of Tumour liberated particles (TLP) having the amino acid sequence comprised within the sequence of the 100 KDa protein of TLP.

According to a preferred embodiment of the invention, said peptide has at least one of the amino acid sequences listed at the end of the specification as Seq ID N1, Seq ID N2 or Seq ID N3. Preferably said peptides are of synthetic origin, alternatively of natural source.

In a further embodiment of the invention, said peptide comprises a cysteine residue at either its carboxylic or aminic terminal group, and a molecule carrier, covalently bound to said residue; preferably said molecule carrier is hemocyanin, most preferably said hemocyanin is obtained from oysters.

Another object of the invention are antibodies able to specifically detect TLP proteins by recognizing an antigenic peptide of Tumour liberated particles (TLP) having the amino acid sequence comprised within the sequence of the 100 KDa protein of TLP.

Preferably said antibodies recognize a peptide having at least one of the amino acid sequences listed at the end of the specification as Seq ID N1, Seq ID N2 or Seq ID N3.

A further object of the invention are diagnostic kits to detect TLP from samples comprising the antibodies of the invention as specific reactants.

Another object of the invention is a method to detect TLP complexes from samples, comprising the steps as follows:
- to immunoprecipitate said sample with a first amount of the serum anti-TLP;
- to evidentiate said TLP complexes from said immunoprecipitated material by reacting the same with a second amount of said serum anti-TLP, and with revealing means of said reaction.

This invention will be described in the following with reference to some explanatory, but not limiting examples, to which are related the annexed figures, wherein.

EXAMPLE 1
Detection and Synthesis of Peptides of the Tlp Protein

The TLP complex is isolated from lung carcinoma extracts, as described in the EP 283 443. The protein is blocked at the amino terminal group and accordingly digested by V8 protease from *Staphylococcus aureus*, using known techniques. One of the obtained peptide fragments shows the sequence as follows: XaaXaaArgThrAsnLysGlu-AlaSerIle.

Two synthetic peptides are synthetised, using the solid phase method, by means of a 430 peptide synthetizer from Applied Biosystems, as described by Bodanszky M., Springer Verlag, New York, N.Y., 1984, having the sequences as shown in the table 1 herebelow:

TABLE 1

5'-ArgThrAsnLysGluAlaSerIleCys-3'

5'-CysArgThrAsnLysGluAlaSerIle-3'

The product identity and purity are confirmed by an analysis of amino acids and HPLC (through a high pressure liquid chromatography procedure).

By using the method described in "Laboratory Techniques in Biochemistry and Molecular Biology" by M. H. V. Van Regermortel, J. P. Brian, S. Muller and S. Plau, Elseviers Publisher, Amsterdam, The Netherlands, 1988, the peptides are linked through the cysteine sulphydryl end groups to the lysine lateral residue of oyster hemocyanin, using the maleinhydrobenzoyl-N-hydrosuccinimide esther (MBS) as reactant.

EXAMPLE 2
Immunization

Four rabbits are injected subcutaneously with 0.5 g of a mixture of the complexes of the Example 1 in 1.5 ml of PBS (phosphate salt buffer) and with 0.5 ml of complete Freund's adjuvant. Incomplete adjuvant as burst injection is administered at two week intervals. Serum samples are picked up each two weeks and subjected to RIA, as described in "Laboratory Techniques in Biochemistry and Molecular Biology", 4th edition, by T. Chard, Elsevier Science Publishers, Amsterdam, The Netherlands, 1990, using 96 well microtitration plates, covered with a known concentration of synthetic peptides as antigens. The plates are incubated at different serum dilution levels, then washed out and treated with iodinized protein A in order to detect the presence of specific antibodies in the serum. The FIG. 1 shows the resulting data of the sampled sera from the four immunized rabbits as above. All sera show an appr. 15,000 cpm radioactivity peak at 1:1,000 dilution, and are able to react also at higher dilutions. The basic levels, obtained with pre-immunized sera as controls, are in the range from 1,000 cpm up to 1,500 cpm, showing a 10:1 ratio at 1:1,000 dilution. The background signal ratio is higher than 20:1 for the 419 and 428 sera.

EXAMPLE 3
Reaction with Sera

Figure 1A:
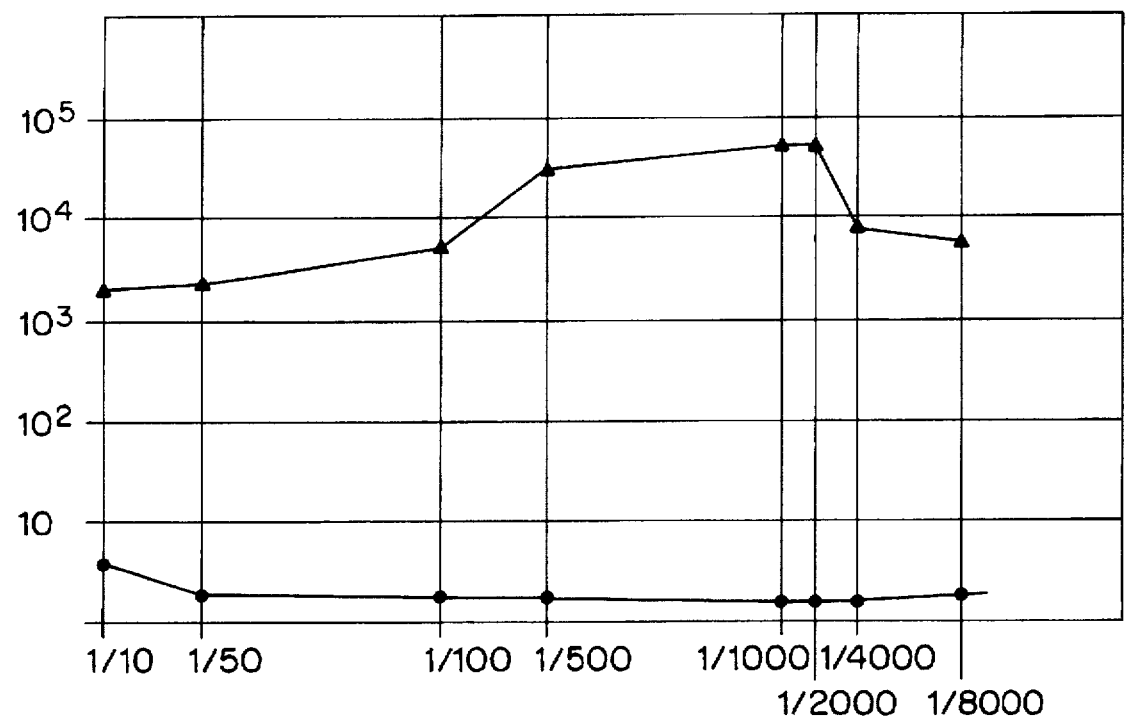
FIGS. 1A-1D show some graphics of RIA immunologic assays of serum samples from 4 rabbits immunized with the peptides described in Seq ID N1, N2 and N3 (A, B, C(419) and D(428)
Figure 1B:
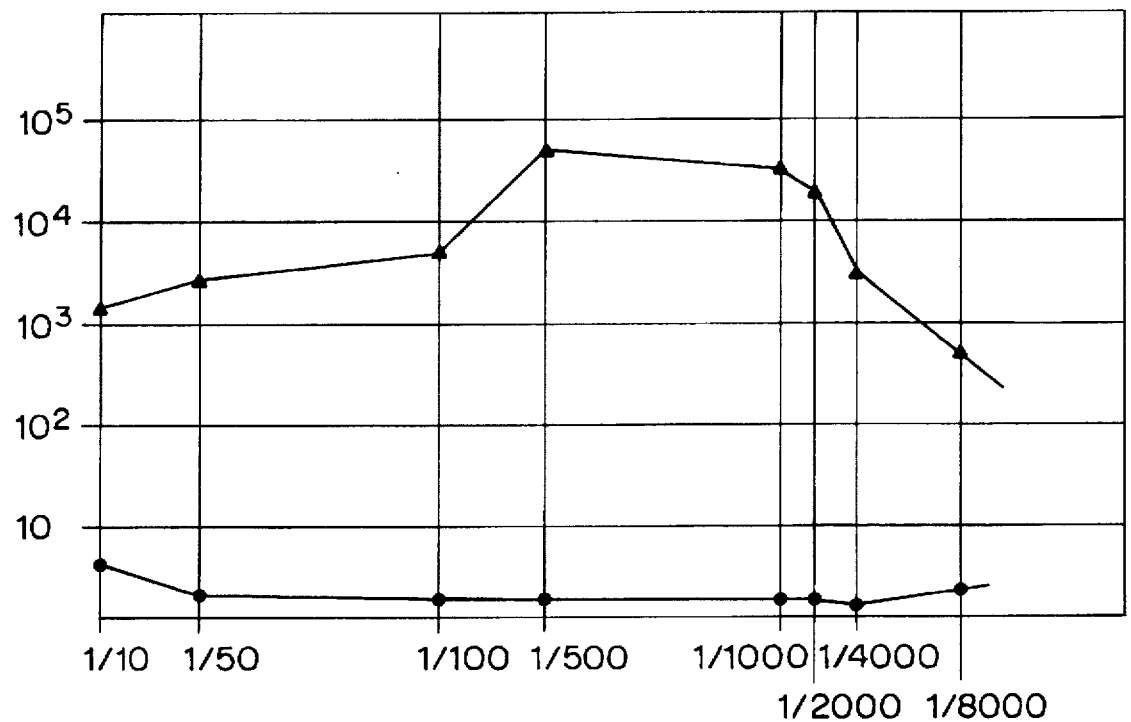
Figure 1C:
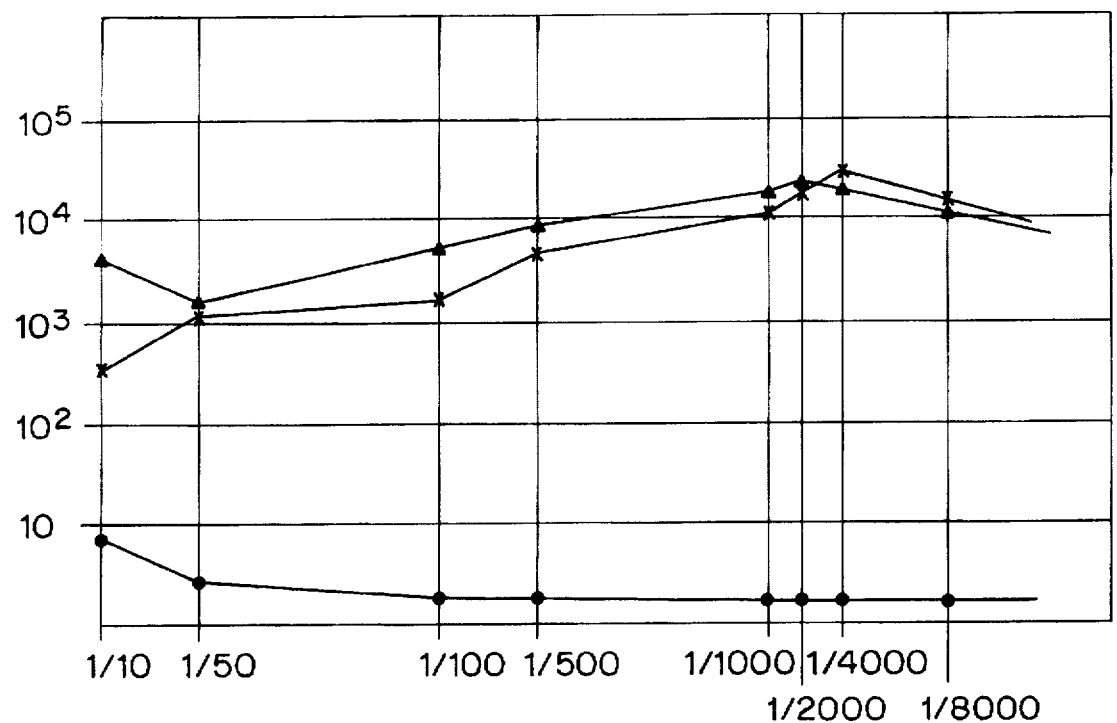
Figure 1D:
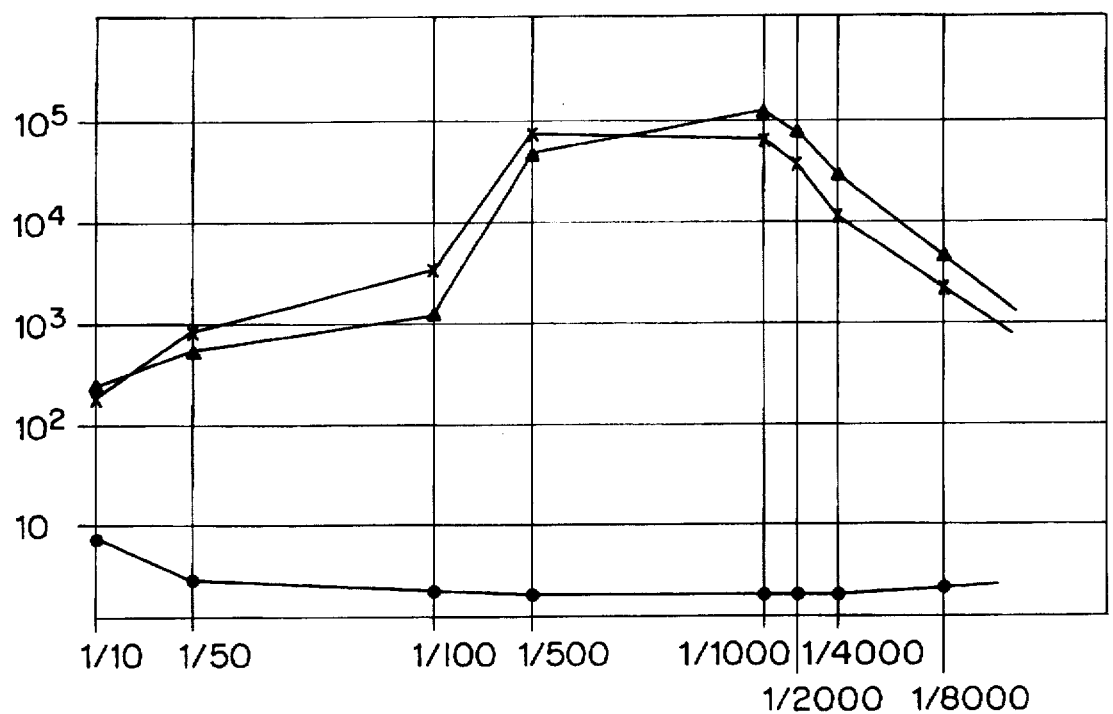
Figure 2A:
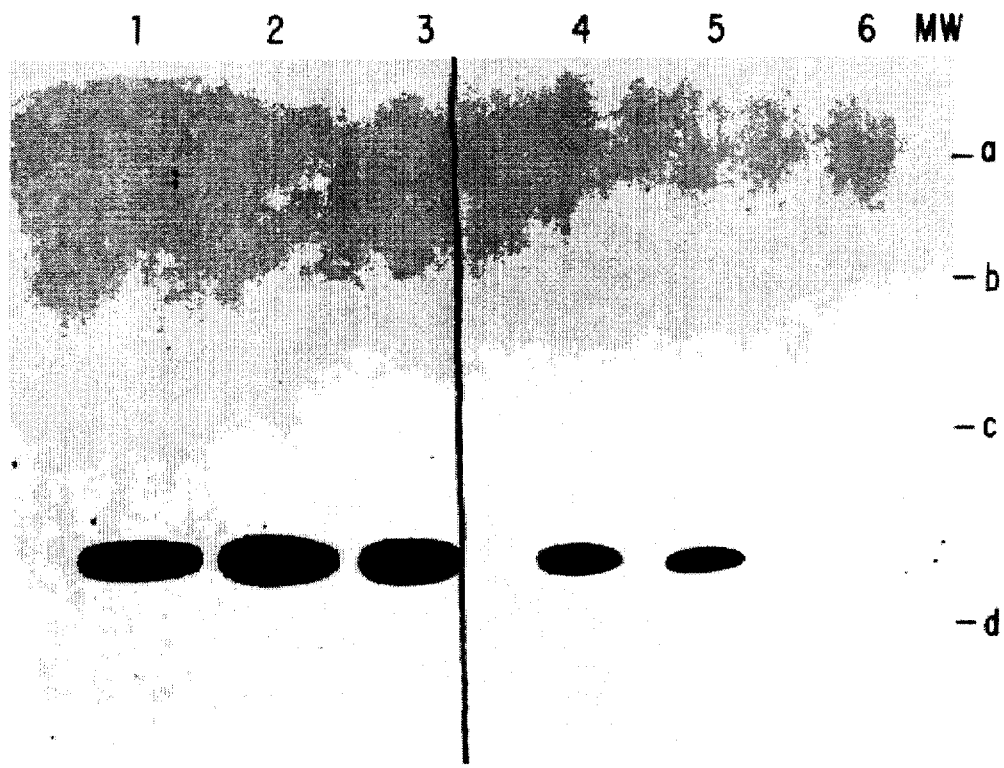
FIG. 2A shows a direct immunoblot, using the sera 419 (1) and 428 (2), as well as previously immunized sera (4-6) on samples of lung extracts.

The 419 and 428 sera are assayed using lung extracts which are obtained, as described in the EP 283 443, by three patients suffering a lung epidermoidal-type carcinoma or an adenocarcinoma, according to "International Classification of Diseases for Oncology, 2nd edition 1990, edited by C. Percy, V. Van Holte and C. Muir, WHO, Geneva (FIG. 2A). Aliquots of said extracts (1 and 4=B.C.; 2 and 5=S.G.; 3 and 6=M.R.) are solubilized in detergent solutions and separated by an electrophoresis procedure according to known methods by polyacrylamide gels. A direct immunoblot is then carried out using the 419 (1) and 428 (2) sera. Two non specific appr. 55 KDa and 35 KDa proteic bands are detected, which are present also when the pre-immunized sera (4–6) are used.

Figure 2B:
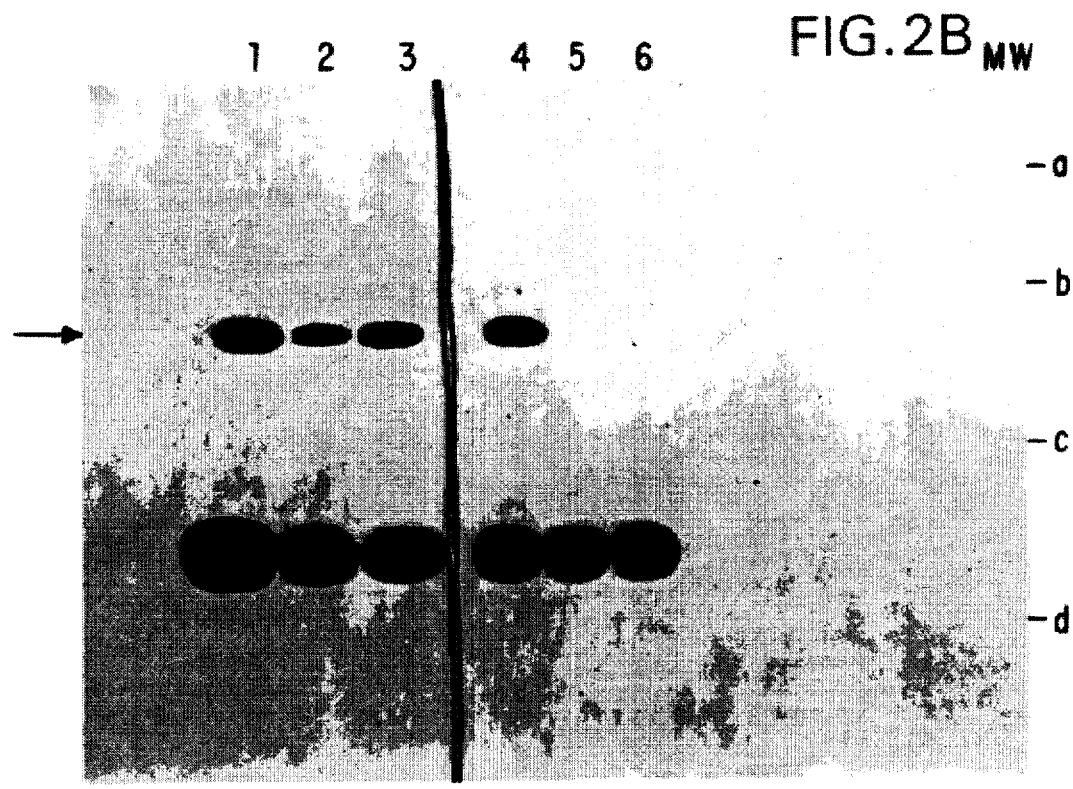
FIG. 2B shows an immunoblot wherein the extracts have been previously immunoprecipitated using the 419 and 428 sera.

Then, the extract are immunologically precipitated with the 419 and 428 sera, using existing techniques, as described by E. Harlow and D. Lane, Cold Spring Harbor Laboratory, Cold Spring Harbor, N.Y. (1988); the immunological precipitated material is separated on gel and used for immunoblot with the same sera. FIG. 2 shows the results, wherein a 100 KDa specific band is detected in all extracts, when assayed both with the 419 serum (1–3) and the 428 serum (4–6). The assayed extract in 1 and 4 shows a very large TLP protein amount.

Figure 2C:
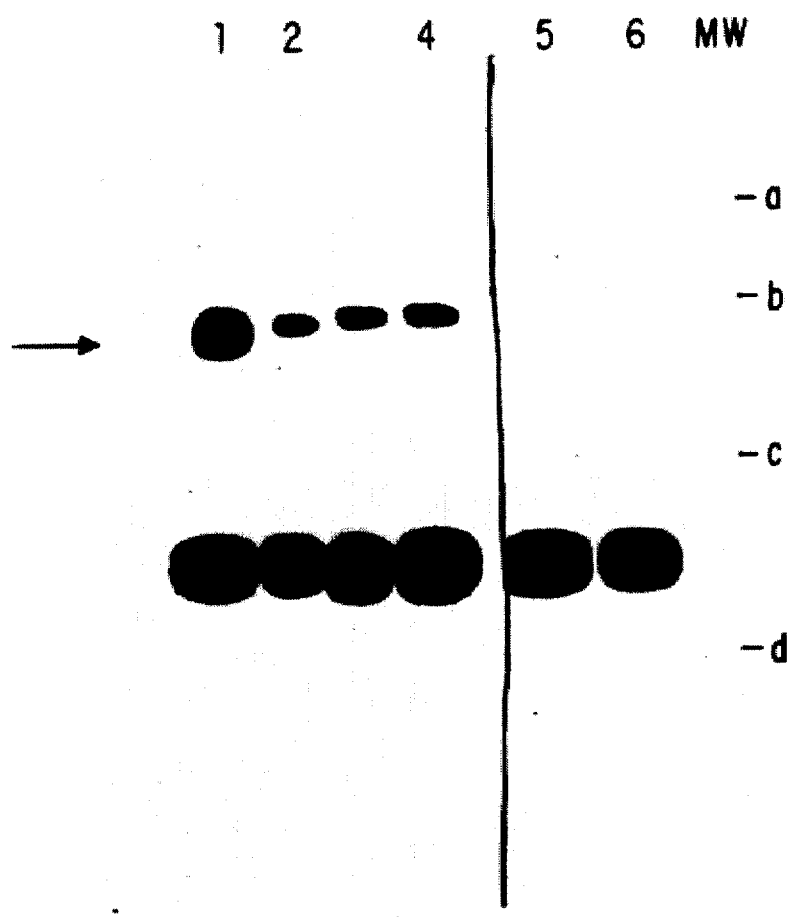
FIG. 2C shows an immunoblot wherein the extracts have been previously immunoprecipitated, as described in the Example 3.

In order to establish whether the reaction is specific, the following control tests are carried out, as shown in FIG. 2C, wherein: line 1 is the BC patient's serum, wherein the 419 immunized serum is used either to immunoprecipitate and to immunoblot; line 2 is obtained using a pre-immunized serum for the immunoprecipitation step and the 419 serum for the immunoblot; line 4 results from using the 419 serum, preincubated with the peptide of Seq ID N1, for the precipitation step and the 419 serum for the immunoblot; line 5 is obtained by using the 419 serum for the immunoprecipitation step and the pre-immunized serum for the immunoblot.

The results confirm that the appr. 100 KDa proteic band specifically reacted with the immunized 419 serum.

I claim:

1. An antigenic peptide of a tumor liberated particle purified from a tumoral tissue, wherein the antigenic peptide is able to induce an immune serum which recognizes a 100 KDa tumor liberated particle, said 100 KDa tumor liberated particle comprising an antigenic amino acid sequence selected from the group consisting of SEQ ID NO. 1: Arg Thr Asn Lys Glu Ala Ser Ile SEQ ID NO. 2: Gly Ser Ala Xaa Phe Thr Asn; and SEQ ID NO. 3: Asn Gln Arg Asn Arg Asp.

2. An antigenic peptide of a Tumour liberated particle according to claim 1 wherein said peptide comprises a cysteine residue at either its carboxylic or aminic terminal group, and a molecule carrier, covalently bound to said residue.

3. An antigenic peptide of a Tumour liberated particle according to claim 2, wherein said molecule carrier is hemocyanin.

4. An antigenic peptide of a Tumour liberated particle according to claim 3, wherein said hemocyanin is hemocyanin from oysters.

* * * * *

UNITED STATES PATENT AND TRADEMARK OFFICE
CERTIFICATE OF CORRECTION

PATENT NO.    : 5,747,643
DATED         : May 5, 1998
INVENTOR(S)   : Tarro

It is certified that error appears in the above-identified patent and that said Letters Patent is hereby corrected as shown below:

Title page,
Item [73], Assignee, "Instituto Farmacoterapico Italiano S.p.A., Italy" should read -- Unihart Corporation, Dublin, Ireland --.

Signed and Sealed this

Eighteenth Day of March, 2003

JAMES E. ROGAN
*Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: NO ( i i i ) ANTI-SENSE: NO ( v i ) ORIGINAL SOURCE:
        ( A ) ORGANISM: Homo sapiens
        ( F ) TISSUE TYPE: Lung carcinoma ( x i ) SEQUENCE DESCRIPTION: SEQ ID NO: 1:

Arg  Thr  Asn  Lys  Glu  Ala  Ser  Ile
        1                         5

( 2 ) INFORMATION FOR SEQ ID NO: 2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens
        ( F ) TISSUE TYPE: Lung carcinoma ( x i ) SEQUENCE DESCRIPTION: SEQ ID NO: 2:

Gly  Ser  Ala  Xaa  Phe  Thr  Asn
        1                         5

( 2 ) INFORMATION FOR SEQ ID NO: 3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens
        ( F ) TISSUE TYPE: Lung carcinoma ( x i ) SEQUENCE DESCRIPTION: SEQ ID NO: 3:

Asn Gln Arg Asn Arg Asp
    1             5